United States Patent [19]

Evans et al.

[11] Patent Number: 5,503,759
[45] Date of Patent: Apr. 2, 1996

[54] MIXTURES OF ALKYLATED AROMATIC AMINES AND PHENOTHIAZINES

[75] Inventors: Samuel Evans, Marly; Stephan Allenbach, Düdingen, both of Switzerland

[73] Assignee: Ciba-Geigy Corporation, Tarrytown, N.Y.

[21] Appl. No.: 359,978

[22] Filed: Dec. 20, 1994

[30] Foreign Application Priority Data

Dec. 23, 1993 [CH] Switzerland ............... 3845/93

[51] Int. Cl.⁶ .................. C10M 135/36; C08K 5/34
[52] U.S. Cl. .................. 252/47.5; 252/47; 252/78.1; 544/35; 544/38; 524/83
[58] Field of Search .......... 544/35, 38; 524/83; 252/47.5, 47

[56] References Cited

U.S. PATENT DOCUMENTS

| | | | |
|---|---|---|---|
| 3,523,910 | 8/1970 | Randell | 524/83 |
| 3,803,140 | 4/1974 | Cook et al. | 524/83 |
| 4,565,834 | 1/1986 | Buysch et al. | 544/35 |
| 4,824,601 | 4/1989 | Franklin | 252/401 |
| 4,897,436 | 1/1990 | Buysch et al. | 524/83 |
| 5,026,846 | 6/1991 | Duchesne | 544/1 |
| 5,059,643 | 10/1991 | Buysch et al. | 544/38 |
| 5,219,892 | 6/1993 | Suhoza | 524/83 |
| 5,413,737 | 5/1995 | Evans | 544/35 |

FOREIGN PATENT DOCUMENTS

| | | |
|---|---|---|
| 2051156 | 3/1992 | Canada . |
| 417036 | 3/1991 | European Pat. Off. . |

OTHER PUBLICATIONS

Chem. Abst. 92–090473 (Month N/A).

*Primary Examiner*—Ellen M. McAvoy
*Attorney, Agent, or Firm*—Michele A. Kovaleski

[57] ABSTRACT

The invention relates to reaction products suitable as antioxidants which are substantially liquid at room temperature and which are obtained by the reaction of olefins with mixtures of diphenylamines and phenothiazines which may be alkylated. These products are obtainable by reacting an olefin of formula $$R_1R_2C=CHR_3 \quad (I)$$

with a mixture of compounds of formulae II and III

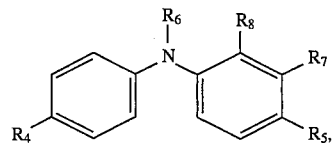

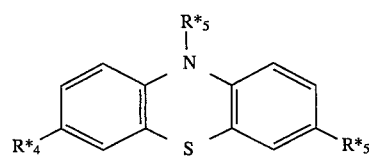

in the presence of an acid catalyst, wherein $R_1$ is hydrogen, $C_1$–$C_{25}$alkyl or phenyl, $R_2$ is $C_1$–$C_{25}$alkyl, benzyl or phenyl, $R_3$ is hydrogen or $C_1$–$C_{12}$alkyl, $R_4$, $R^*_4$, $R_5$ and $R^*_5$ are each independently of one another hydrogen, $C_1$–$C_{25}$alkyl, $C_5$–$C_{12}$cycloalkyl, benzyl, α-methylbenzyl or α,α-dimethylbenzyl, and $R_6$ and $R^*_6$ are each independently of the other hydrogen, $C_1$–$C_{18}$alkyl, $C_1$–$C_4$alkenyl, benzyl or a radical of formula —CH($R_9$)—CH($R_{10}$)—S—$R_{11}$, and $R_7$ and $R_8$ are hydrogen, or together form a divalent group

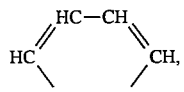

$R_9$ and $R_{10}$ are each independently of the other hydrogen, phenyl or $C_1$–$C_{12}$alkyl, $R_{11}$ is $C_4$–$C_{18}$alkyl, phenyl or —$(CH_2)_a$—CO—O$R_{12}$, a is 1 or 2, and $R_{12}$ is $C_1$–$C_{18}$alkyl.

22 Claims, No Drawings

MIXTURES OF ALKYLATED AROMATIC AMINES AND PHENOTHIAZINES

The invention relates to novel reaction products comprising alkylated diphenylamines and phenothiazines which are suitable as antioxidants, to compositions containing said reactions products, to the use thereof and to a process for their preparation.

Liquid mixtures of amino antioxidants have been used for some time, in particular in lubricating oils for combustion engines. In particular, EP-A-0 149 422 discloses a mixture of unsubstituted diphenylamine and diphenylamine differently substituted by alkyl groups, and EP-A-0 475 904 discloses a composition containing phenothiazine(s) resulting from the reaction of such mixtures with sulfur.

Furthermore, EP-A-0 275 910 discloses the preparation of mixtures consisting of diphenylamine and phenothiazine compounds which are substituted by phenolic groups.

Surprisingly, it has now been found that the process described hereinafter makes it possible to obtain a liquid additive mixture which is particularly suitable for use in lubricant compositions and, most particularly, for the control of deposit formation.

Accordingly, the invention relates to the reaction product obtainable from the reaction of an olefin of formula

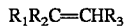

$$R_1R_2C=CHR_3 \quad (I)$$

with a mixture of compounds of formulae II and III

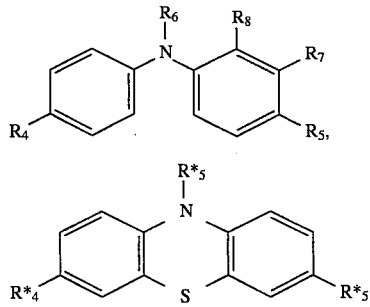

in the presence of an acid catalyst, wherein $R_1$ is hydrogen, $C_1$–$C_{25}$alkyl or phenyl, $R_2$ is $C_1$–$C_{25}$alkyl, benzyl or phenyl, $R_3$ is hydrogen or $C_1$–$C_{12}$alkyl, $R_4$, $R^*_4$, $R_5$ and $R^*_5$ are each independently of one another hydrogen, $C_1$–$C_{25}$alkyl, $C_5$–$C_{12}$cycloalkyl, benzyl, α-methylbenzyl or α,α-dimethylbenzyl, and $R_6$ and $R^*_6$ are each independently of the other hydrogen, $C_1$–$C_{18}$alkyl, $C_3$–$C_4$alkenyl, benzyl or a radical of formula —CH($R_9$)—CH($R_{10}$)—S—$R_{11}$, and $R_7$ and $R_8$ are hydrogen, or together form a divalent group

TABLE I

| | Deposit and Oxidation Panel Test | | |
|---|---|---|---|
| Product according to | Concentration | Deposit | |
| Example | [% by weight] | weight [mg] | visual |
| 3 | 0.6 | 21 | 10 |
| 4 | 0.6 | 22 | 10 |
| no addition | — | 145 | 15 |

$R_9$ and $R_{10}$ are each independently of the other hydrogen, phenyl or $C_1$–$C_{12}$alkyl, $R_{11}$ is $C_4$–$C_{18}$alkyl, phenyl or —(CH$_2$)$_a$—CO—OR$_{12}$, a is 1 or 2, and $R_{12}$ is $C_1$–$C_{18}$alkyl.

Alkyl radicals ($R_1$ to $R^*_6$ and $R_9$ to $R_{12}$) defined as $C_1$–$C_{12}$alkyl, $C_1$–$C_{18}$alkyl, $C_4$–$C_{18}$alkyl or $C_1$–$C_{25}$alkyl may be straight-chain or branched and, depending on the indicated number of carbon atoms, are typically methyl, ethyl, propyl, isopropyl, n-butyl, isobutyl, t-butyl, pentyl, isopentyl, hexyl, heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl, eicosyl or heneicosyl. Where these substituents hereinafter are groups containing a lower number of carbon atoms, the corresponding examples may be likewise inferred from the above list.

The alkyl radicals, except $R_2$, $R_4$, $R^*_4$, $R_5$, $R^*_5$ and $R_{11}$, contain preferably 1 to 12, more particularly 1 to 6 and, most preferably, 1 to 4 carbon atoms. $R_2$, $R_4$, $R^*_4$, $R_5$ and $R^*_5$ defined as alkyl preferably contain more than 3 carbon atoms, and $R_3$, $R_9$ and $R_{10}$ preferably contain 1 to 6 carbon atoms.

$C_5$–$C_{12}$Cycloalkyl is typically cyclopentyl, cyclohexyl, cyclooctyl, cyclododecyl. (Cycloalkyl radicals containing 5 to 8 and, more particularly, 5 or 6 carbon atoms are preferred. Cyclohexyl is most preferred.)

$C_3$–$C_4$Alkenyl may conveniently be allyl or methallyl.

Advantageous products obtainable by the reaction described above are those wherein $R_1$ is hydrogen or $C_1$–$C_6$alkyl, $R_2$ is $C_1$–$C_{18}$alkyl or phenyl, $R_3$ is hydrogen or $C_1$–$C_{12}$alkyl, $R_4$, $R^*_4$, $R_5$, $R^*_5$ are hydrogen, $C_4$–$C_{18}$alkyl, cyclohexyl, benzyl, α-methylbenzyl or α,α-dimethylbenzyl, and $R_6$ and $R^*_6$ are each independently of the other hydrogen, methyl, allyl or benzyl.

Those products are preferred, wherein $R_1$ is hydrogen or $C_1$–$C_4$alkyl, $R_2$ is $C_1$–$C_{18}$alkyl, and $R_3$ is hydrogen or $C_1$–$C_4$alkyl.

Particularly preferred products are those wherein $R_1$ and $R_3$ are hydrogen or methyl, and $R_2$ is $C_1$–$C_{12}$alkyl.

Further very particularly preferred products are those wherein $R_4$, $R^*_4$, $R_5$, and $R^*_5$ are hydrogen.

Suitable olefins of formula I are preferably alpha-olefins containing 1 to 20 carbon atoms and, most preferably, diisobutylene. Accordingly, $R_3$ is preferably hydrogen.

The further features of the compositions are substantially governed by the composition of the reaction mixtures and the chosen process conditions.

The starting mixtures may conveniently have the following composition: The molar ratio of compound of formula II: compound of formula III is conveniently from 5:95 to 95:5, preferably from 70:30 to 30:70, more particularly from 70:30 to 95:5 and, most preferably, from 80:20 to 90:10.

The compound of formula I is conveniently used in an amount of 0.5 to 4 mol per mol of the mixture consisting of the compounds of formulae II and III, preferably in an amount of 1 to 3, more preferably of 1 to 2 mol per mol of the mixture consisting of the compounds of formulae II and III.

The acid catalyst may be typically used in an amount of 1 to 50% by weight, preferably of 5 to 20% by weight and, most preferably, 7 to 15% by weight, based on the mixture consisting of the compounds of formulae II and III, or, if the acid catalyst is a Brønsted acid or a Lewis acid, in an amount of 0.002 to 10% mol, preferably of 0.1 to 5% mol.

The acid catalyst is preferably an acid clay of the bentonire or montmorillonite type, as described in more detail hereinafter.

The reaction can be carried out with or without solvents or diluents, preferably without. However, the use of a solvent or diluent may be convenient, for example for the elimination of reaction heat. If a solvent is used, then it should be inert under the reaction conditions and have a suitable boiling point. Suitable solvents are, for example, hydrocarbons or halogenated hydrocarbons, polar aprotic solvents and alcohols. Illustrative examples are petroleum ether fractions, which are preferably higher-boiling, toluene, dichlorobcnzene; tetrahydrofuran (THF), dimethylformamide (DMF), dimethylacetamide (DMA), hexamethylphosphoric acid triamide (HMPTA), dimethyl sulfoxide (DMSO) and tetramethylurea (TMU), and also pyridine or alkylpyfidines; as well as alcohols such as butanol, glycol or diethylene glycol.

The reaction temperature may vary over a wide range, e.g. from 60°–250° C., preferably from 110°–200° C., more particularly from 130°–195° C. and, most preferably, from 160°–180° C.

The reaction can be catalysed homogeneously or heterogeneously.

Suitable catalysts are Brønsted acids, Lewis acids, aluminium silicates, ion exchange resins, zeolites, naturally occuring sheet silicates (for example "acid clays" such as Fuller's earth) or modified sheet silicates.

Illustrative examples of suitable Brønsted acids are acids of inorganic or organics salts, typically hydrochloric acid, sulfuric acid, phosphoric acid, methanesulfonic acid, p-toluenesulfonic acid, or carboxylic acids such as acetic acid. p-Toluenesulfonic acid is particularly suitable.

Illustrative examples of suitable Lewis acids are tin tetrachloride, aluminium chloride, zinc chloride or boron trifluoride etherate. Tin tetrachloride and aluminium chloride are particularly suitable.

Illustrative examples of suitable aluminium silicates are those that are widely used in the petrochemical industry and are also known as amorphous aluminium silicates. These compounds contain c. 10–30% of silicon monoxide and 70–90% of aluminium oxide. A particularly preferred aluminium silicate is HA-HPV® available from Ketjen (Akzo).

Illustrative examples of suitable ion exchange resins are typically styrene-divinylbenzene resins which additionally carry sulfonic acid groups, for example Amberlite 200® and Amberlyst® available from Rohm and Haas, or Dowex 50® available from Dow Chemicals; perfluorinated ion exchange resins such as Nafion H® sold by DuPont; or other superacidic ion exchange resins such as those described by T. Yamaguchi, Applied Catalysis, 61, 1–25 (1990) or M. Hino et al., J. Chem. Soc. Chem. Commun. 1980, 851–852.

Suitable zeolites are typically those widely used in petrochemistry as cracking catalysts and known as crystalline silicon-aluminium oxides of different crystal structure. Particularly preferred zeolites are the Faujasites available from Union Carbide, for example Zeolith X®, Zeolith Y® and ultrastable Zeolith Y® ; Zeolith Beta® and Zeolith ZSM-12® available from Mobil Oil Co.; and Zeolith Moralenit® available from Norton.

Suitable naturally occurring sheet silicates are also termed "acid clays" and typically include bentonites or montmorillonites, which are degraded, ground, treated with mineral acids and calcined industrially. Particularly suitable natural sheet silicates are Fulcat® types available from Laporte Adsorbents Co., for example Fulcat 22A®, Fulcat 22B®, Fulcat 20® or Fulcat 40®; or the Fulmont® types available from Laporte Adsorbents Co., for example Fulmont XMP-3® or Fulmont XMP-4®. A particularly preferred catalyst for the process of this invention is Fulcat 22B®, an acid-activated montmorillonite having 4% of free moisture and an acid titer of 20 mg KOH/g. However, the other Fulcat® types and Fulmont® types also belong to this preferred class, because there are only minor differences between the individual types, as for example in the number of acid centres.

Modified sheet silicates are also termed "pillared clays" and are derived from the above described naturally occurring sheet silicates by additionally containing between the silicate layers oxides of e.g. zirconium, iron, zinc, nickel, chromium, cobalt or magnesium, or elements of the rare earths. This type of catalyst is described in the literature, inter alia by J. Clark et. al., J. Chem. Soc. Chem. Commun. 1989, 1353–1354 and is widely used, but is available from only a very few firms. Particularly preferred modified sheet silicams typically include Envirocat EPZ-10®, Envirocat EPZG® or Envirocat EPIC® available from Contract Chemicals.

The novel reaction products are admirably suited for stabilising organic materials against light-induced, thermal and/or oxidalive degradation. Accordingly, the invention also relates to compositions containing an organic material susceptible to such degradation reactions, to the novel reaction product and to the use of novel reaction products for stabilising organic materials against the cited types of degradation.

The novel reaction products may in particular be used for stabilising natural, semi-synthetic or synthetic polymers, more particularly thermoplastics and elastomers and functional fluids, in particular lubricants, machining fluids and hydraulic fluids. Illustrative examples of such substrates will be found in the following list of suitable materials:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1 ), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose buryrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compositions of this invention conveniently contain the novel reaction products in amounts of 0.01 to 10% by weight, typically of 0.05 to 5% by weight, preferably of 0.05 to 3% by weight, but most preferably of 0.1 to 2% by weight. The compositions may contain one or more than one of these novel reaction products, and the percentages by weight are based on the total amount of these novel reaction products. The amounts refer to the total weight of organic material, without the novel reaction products.

Incorporation in the materials can be effected by blending them with, or by applying thereto, the novel reaction products and further optional additives by methods which are commonly used in the art. If the organic materials are polymers, especially synthetic polymers, the incorporation can be effected before or during the fabrication of shaped articles or by applying the dissolved or dispersed novel reaction products to the polymer, with or without subsequent evaporation of the solvent. In the case of elastomers, these may also be stabilised as lattices. A further means of blending the novel reaction products into polymers consists in adding said reaction products before, during or directly after the polymerisation of the corresponding monomers or before crosslinking. The novel reaction products can also be added in encapsulated form (i.e. in waxes, oils or polymers). If the reaction products are added before or during polymerisation, they can also act as regulators for the chain length of the polymers (chain terminator).

The novel reaction products or mixtures thereof can also be added in the form of a masterbatch containing these compounds to the polymers to be stabilised, typically in a concentration of 2.5 to 25% by weight.

The novel reaction products may conveniently be incorporated by the following methods:

as emulsion or dispersion (e.g. to latices or emulsion polymers)

as dry mixture during the mixing of additional components or polymer mixtures direct addition to the processing apparatus (e.g. extruder, closed mixer etc.)

as solution or melt.

The novel polymer composition may be used in different forms of presentation, typically as sheets, filaments, ribbons, mouldings, profiles or binders for paints and varnishes, adhesives or putties.

The invention also relates to a process for stabilising organic material, in particular thermoplastic polymers, elastomers or functional fluids, most particularly lubricants, against oxidative, thermal and/or light-induced degradation, which comprises adding or applying to said material novel reaction products as stabilisers.

The novel reaction products are particularly suitable for imparting enhanced performance properties to functional fluids. The surprisingly good antioxidative and deposit control action merits special mention. Accordingly, the invention also relates to compositions comprising a functional fluid and at least one compound of the general formula I, as described above.

Illustrative examples of functional fluids are lubricants, hydraulic fluids and machining fluids. Lubricating greases also fall under the functional fluids.

Suitable lubricants may be those based on mineral or synthetic oils or mixtures thereof, or on vegetable and animal oils, fats and waxes. The lubricants are known to the skilled person and described in the relevant literature, for example in Dieter Klamann, "Schmierstoffe and verwandte Produkte" (Verlag Chemie, Weinheim, 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie", vol. 13, pages 85–94 (Verlag Chemie, Weinheim, 1977).

The lubricants are preferably oils and fats, based on a mineral oil. The oils are preferred. The mineral oils are based preferably on hydrocarbon compounds.

Synthetic lubricants typically comprise lubricants based on aliphatic or aromatic carboxylates, polymeric esters, polyalkylene oxides, phosphates, poly-α-olefins or silicones, on a diester of a divalent acid with a monohydric alcohol, for example dioctyl sebacate or dinonyl adipate, on a triester of trimethylolpropane with a monovalent acid or with a mixture of such acids, for example trimethylolpropane tripelargonate, trimethylolpropane tricaprylate or mixtures thereof, on a tetraester of pentaerythritol with a monovalent acid or with a mixture of such acids, for example pentaerythritol tetracaprylate, or on a complex ester of monovalent and divalent acids with polyhydric alcohols, for example a complex ester of trimethylolpropane with caprylic and sebacic acid or of a mixture therof. Especially suitable are, in addition to mineral oils, for example poly-α-olefins, ester-based lubricants, phosphates, glycols, polyglycols and polyalkylene glycols, and mixtures thereof with water.

Suitable vegetable oils are the oils, fats and waxes which may be obtained from olives, palms, palm nuts, beet, rape, linseeds, groundnuts, soybeans, cotton seeds, castor oil plants, sunflower seeds, pumpkin seeds, coconuts, maize or their modified forms such as sulfated or epoxidised oils, for example epoxidised soybean oil, as well as mixtures of these substances. Illustrative examples of animal oils, fats and waxes which may be used as lubricants are tallows, fish oils, sperm oils, neat's foot oil, lard oils and the modified forms and mixtures thereof.

Suitable machining fluids are rolling oils, drawing oils and cutting oils which are mainly based on the mineral and synthetic oils described above and which may also be in the form of oil-in-water emulsions or water-in-oil emulsions, as is also the case with hydraulic fluids. Further functional fluids may suitably be compressor oils and spinning preparations.

The novel reaction products described above may be present in the functional fluid in amounts of typically 0.01 to 10% by weight, conveniently of 0.05 to 5% by weight, preferably of 0.05 to 3% by weight and, most preferably, of 0.5 to 1.5% by weight, based on the composition.

The compounds of formula I may be mixed with the functional fluid in a manner known per se. The compounds are readily soluble in oils. It is also possible to prepare a masterbatch, which can be diluted in accordance with the consumption to suitable concentrations with the appropriate functional fluid.

In addition to the novel products or mixtures, the novel compositions may also contain further additives, in particular when they contain organic and, preferably, synthetic polymers. Illustrative examples of these additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxy-anisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(αmethylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxy-dibenzyl ether, octadecyl-4-hydroxy-3,5-dimethylbenzylmercaptoacetate, tris-(3,5-di-tert-butyl-4-hydroxbenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-di-methylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or poly- hydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β(3,5-dicyclohexyl-4-hydroxyphenyl)propionic acid with mono- or poly- hydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1.2-(2'-Hydroxyphenyl))benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tertbutylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypipefidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxy-phenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-di-acetyladipoyl dihydrazide, N,N'-bis(salicyloyl)oxalyl dihydrazide, N,N'-bis(salicyloyl)-thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentacrythritol diphosphite, bis(2,6-di-tert-butyl-4-methylphenyl)-pentaerythritol diphosphite, diisodecyloxypentacrythritol diphosphite, bis(2,4-di-tert-butyl-6-methylphenyl)pentaerythritol diphosphite, bis(2,4,6-tris(tert-butylphenyl)pentacrythritol diphsophite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of βthiodipropionic acid, for example the lauryl, stearyl, myristyl or tridecyl esters, mercaptobenzimidazole or the zinc salt of 2-mereaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244, 5,175,312, 5,216,052, 5,252,643, 4,316,611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

If the novel compositions are based on functional fluids, in particular on lubricants and hydraulic fluids or machining fluids, then they may also comprise further additives which are added for the enhancement of certain performance properties. Such additional additives comprise for example further antioxidants, metal deactivators, rust inhibitors, viscosity index improvers, pour-point depressants, disperants/surfactants and extreme pressure and antiwear additives. Illustrative examples of these additives are:

Examples of phenolic antioxidants: These are as in the above items 1.1 to 1.17.

Examples of aminic antioxidants:

N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoyl-aminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N', N'-tetramethyl-4,4'-diaminodiphenylmethane, 1,2-bis[(2-methyl-phenyl)amino]ethane, 1,2-bis-(phenylamino)propane, (o-tolyl)biguanide, bis[4-(1',3'-dimethylbutyl)phenyl]amine, tertoctylated N-phenyl-1-naphthylamine, a mixture of mono- and dialkylated tert-butyl/tertoctyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5, 12-dihydroxy-3,7,10,14-tetrathiahexadecane.

Examples of metal deactivators, for example for copper, are:
a) Benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2, 4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-carboxymethyl-1-dodecyl-3-methylglycerol and the amine salts thereof.

b) Nitrogen-containing compounds, for example:

I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.

II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylate and alkylated naphthalene derivatives.

Examples of dispersants/surfactants are:

Polybutenylsuccinic amides or -imides, polybutenylphosphonic acid derivatives and basic magnesium, calcium and barium sulfonates and phenolates.

Examples of extreme pressure and antiwear additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio] propionate, triphenyl thiophosphate (triphenylphosphorothioate), tris(alkylphenyl) phosphorothioate and mixtures thereof (for example tris(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris [isooctyl 2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The present invention also relates to the use of novel reaction products for stabilising organic material susceptible to oxidative, thermal and/or light-induced degradation, in particular natural or (semi-)synthetic polymers or functional fluids, most particularly lubricants. The compounds are particularly effective as antioxidants and deposit control agents in functional fluids, as mentioned above.

The preferred novel reaction products described above lead to preferred compositions.

The invention also relates to a process for the preparation of compositions by means of the process described at the outset. The starting materials are commercially available or can be prepared by known methods.

The following Examples further illustrate the invention without, however, limiting it. Parts and percentages are by weight, if not otherwise stated.

EXAMPLE 1

In a three-necked flask equipped with reflux condenser, thermometer, magnetic stirrer and water separator, 148.1 g (0.875 mol) of diphenylamine, 24.9 g (0.125 mol) of phenothiazine and 17.6 g of Fulcat 22B® are fused at 100° C. in 76.2 g (0.679 mol) of diisobutylene in a weak stream of nitrogen. The mixture is heated over one hour to 175° C. (strong reflux), and simultaneously c. 2 ml of water are collected in the water separator. Further 100 g (0.891 mol) of diisobutylene are added dropwise over c. 4 h, such that the temperature is 165°–175° C. The batch is stirred at 165°–175° C. for c. 5 h until the concentration of diphenylamine has fallen below about 4% of the initial concentration.

The batch is cooled to c. 90° C. and filtered to remove the catalyst. Excess diisobutylene (c. 50 g) is distilled off over 2 hours at 80° C. under reduced pressure (c. 0.01 torr).

285 g of a mobile, substantially clear oil are obtained.

Analysis: found 84.22% C, 9.8% H, 4.58% N and 1.36% S

EXAMPLE 2

In a three-necked flask equipped with reflux condenser, thermometer, magnetic stirrer and water separator, 160.8 g (0.950 mol) of diphenylamine, 10.0 g (0.050 mol) of phenothiazine and 17.0 g of Fulcat 22B® are fused at 100° C. in 76.2 g (0.679 mol) of diisobutylene in a weak stream of nitrogen. The mixture is heated over one hour to 175 ° C. (strong reflux), and simultaneously c. 2 ml of water are collected in the water separator. Further 100 g (0.891 mol)

of diisobutylene are added dropwise over c. 3 h, such that the temperature is 165°–175° C. The batch is stirred for c. 3 hours at 165°–175° C. until the concentration of diphenylamine has fallen below about 4% of the initial concentration.

The batch is cooled to c. 90° C. and filtered to remove the catalyst. Excess diisobutylene (c. 34 g) is distilled off over 2 hours at 80° C. under reduced pressure (c. 0.01 torr).

274 g of a mobile, substantially clear oil are obtained.

Analysis: found 84.99% C, 9.9% H, 4.96% N and 0.55% S

EXAMPLE 3

In a three-necked flask equipped with reflux condenser, magnetic stirrer and water separator, 135.4 g (0.80 mol) of diphenylamine, 40.0 g (0.20 mol) of phenothiazine and 17.0 g of Fulcat 22B® are fused at 100° C. in 76.2 g (0.679 mol) of diisobutylene in a weak stream of nitrogen. The mixture is heated over one hour to 175° C. (strong reflux), and simultaneously c. 2 ml of water are collected in the water separator. Further 100 g (0.891 mol) of diisobutylene are added dropwise over c. 3 h, such that the temperature is 165°–175° C. The batch is stirred for c. 4 h at 165°–175° C. until the concentration of diphenylamine has fallen below about 4% of the initial concentration.

The batch is cooled to c. 90° C. and filtered to remove the catalyst. Excess diisobutylene (c. 28 g) is distilled of over 2 hours at 80° C. under reduced pressure (c. 0.01 torr).

291 g of a mobile, substantially clear oil are obtained.

Analysis: found 83.85% C, 9.74% H, 4.43% N and 2.11% S

EXAMPLE 4

In a three-necked flask equipped with reflux condenser, thermometer, magnetic stirrer and water separator, 145.8 g (0.861 mol) of diphenylamine, 27.6 g (0.139 mol) of phenothiazine and 17.0 g of Fulcat 22B® are fused at 100° C. in 76.2 g (0.679 mol) of diisobutylene in a weak stream of nitrogen. The mixture is heated over one hour to 175° C. (strong reflux), and simultaneously c. 2 ml of water are collected in the water separator. Further 100 g (0.891 mol) of diisobutylene are added dropwise over c. 3 h, such that the temperature is 165°–175° C. The batch is stirred for c. 4 h at 165°–175° C. until the concentration of diphenylamine has fallen below about 4% of the initial concentration.

The batch is cooled to c. 90° C. and filtered to remove the catalyst. Excess diisobutylene (c. 27 g) is distilled off over 2 hours at 80° C. under reduced pressure (c. 0.01 torr).

295 g a mobile, substantially clear oil are obtained.

Analysis: found 84.39% C, 9.86% H, 4.73% N and 1.49% S

EXAMPLE 5

In a three-necked flask with reflux condenser, thermometer, magnetic stirrer and water separator, 67.6 g (0.4 mol) of diphenylamine, 20.1 g (0.1 mol) of phenothiazine and 8.8 g of Fulcat 22B® are added to 40 ml of toluene at 100° C. (heat bath) and heated over one hour to 165° C. Simultaneously, c. 1 ml of water is collected in the water separator. Over c. 1 hour, 168.3 g (1.0 mol) of 1-dodecene are added dropwise to the batch, such that the temperature does not fall below 165° C. The batch is stirred for c. 12 h at 165°–175° C. until the concentration of diphenylamine has fallen below about 4% of the initial concentration.

The batch is cooled to c. 90° C. and filtered to remove the catalyst. Excess 1-dodecene is distilled off over 2 hours at 80° C. under reduced pressure (c. 0.01 tort).

99 g of a brown oil are obtained.

Analysis: found 83.94% C, 11.26% H, 3.29% N and 1.57% S

Gas chromatography (GC): DPA content in the product:

EXAMPLE 6

In a three-necked flask equipped with reflux condenser, thermometer, magnetic stirrer and water separator, 87.7 g (0.4 mol) of phenyl-α-naphthylamine (PANA), 20.1 g (0.1 mol) of phenothiazine and 8.8 g of Fulcat 22B® are added to 40 ml of toluene at 100° C. (heating bath) under nitrogen. The mixture is heated over one hour to 165 ° C. Simultaneously, c. 1 ml of water is collected in the water separator. Over c. 1 hour, 168 g (1.0 mol) of 1-dodecene are added dropwise to the batch, such that the temperature does not fall below 165° C. The batch is stirred for c. 12 hours at 165°–175° C. until the concentration of PANA has fallen below about 4% of the initial concentration.

The batch is cooled to c. 90° C. and filtered to remove the catalyst. Excess 1-dodecene is distilled off over 2 hours at 80° C. under reduced pressure (c. 0.01 torr).

189 g of a brown oil are obtained.

Analysis: found 85.10% C, 9.97% H, 3.21% N and 1.51% S GC: PANA content in the product: about 1%

EXAMPLE 7

In a three-necked flask equipped with reflux condenser, thermometer, magnetic stirrer and water separator, 16.9 g (0.1 mol) of diphenylamine, 39.9 g (0.1 mol) of phenothiazine and 6 g of Fulcat 22B® are added to 40 ml of toluene at 100° C. (heating bath) and heated over one hour to 165° C. Simultaneously, c. 1/2 ml of water are collected in the water separator. Over c. 1 hour, 75.8 g (0.6 mol) of tripropylene are added dropwise to the batch, such that the temperature does not fall below 165° C. The batch is stirred for c. 5 hours at 165°–175° C. until the concentration of diphenylamine has fallen below about 4% of the initial concentration.

The batch is cooled to c. 90° C. and filtered to remove the catalyst. Excess tripropylene is distilled off over 2 hours at 80° C. under reduced pressure (c. 0.01 torr).

94 g of a brown oil are obtained.

Analysis: found 80.30% C, 9.30% H, 4.30% N and 6.14% S GC: DPA content: 3.2%; phenothiazine content: 4.1%

EXAMPLE 8

Deposit and Oxidation Panel Test (DOPT)

The Deposit and Oxidation Panel Test is a modified version of a method of testing engine oils, especially diesel engine oils, which has been described by G. Abellaneda et al., IIIe Symposium CEC, 1989, 61 New Cavendish Street, London WIM8AR, England. The object is to test the suitability of the stabilised oils to prevent deposits on the piston.

In an oxidising atmosphere, oil is dripped at a defined rate onto a clean, inclined hot metal plate (panel) which has been weighed beforehand, so as to produce a film of oil. The test duration is 20 hours, the temperature on the panel is 260° C., the air flow is 9.7 l/h and the oil flow is 1 ml/min. The humid atmosphere is enriched with 460 ppm of $NO_2$ and 25 ppm of $SO_2$.

After the test the panel is immersed in petroleum ether to remove the oil, dried, weighed, and assessed visually to determine whether a hard deposit has formed and how the residue is coloured. The lower the weight of the residue and the visual assessment value, the better the result. Commercially available low reference CCMC diesel engine oil is used as lubricating oil.

The stabiliser indicated in Table I is blended with this prepared oil in an amount of 0.6% by weight, based on said oil and subjected to a DOPT.

TABLE I

| Deposit and Oxidation Panel Test | | | |
|---|---|---|---|
| Product according to | Concentration | Deposit | |
| Example | [% by weight] | weight [mg] | visual |
| 3 | 0.6 | 21 | 10 |
| 4 | 0.6 | 22 | 10 |
| no addition | — | 145 | 15 |

What is claimed is:

1. A reaction product obtainable by the reaction of an olefin of formula $$R_1R_2C=CHR_3 \quad (I)$$

with a mixture of compounds of formulae II and III

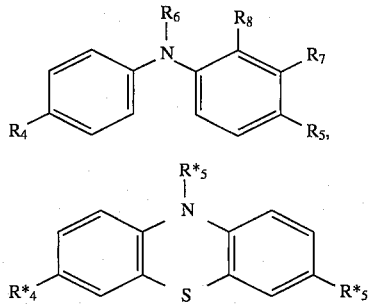

in the presence of an acid catalyst, wherein $R_1$ is hydrogen, $C_1$–$C_{25}$alkyl or phenyl, $R_2$ is $C_1$–$C_{25}$alkyl, benzyl or phenyl, $R_3$ is hydrogen or $C_1$–$C_{12}$alkyl, $R_4$, $R^*_4$, $R_5$ and $R^*_5$ are each independently of one another hydrogen, $C_1$–$C_{25}$alkyl, $C_5$–$C_{12}$cycloalkyl, benzyl, α-methylbenzyl or α,α-dimethylbenzyl, and $R_6$ and $R^*_6$ are each independently of the other hydrogen, $C_1$–$C_{18}$alkyl, $C_3$–$C_4$alkenyl, benzyl or a radical of formula —CH($R_9$)—CH($R_{10}$)—S—$R_{11}$, and $R_7$ and $R_8$ are hydrogen, or together form a divalent group

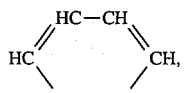

$R_9$ and $R_{10}$ are each independently of the other hydrogen, phenyl or $C_1$–$C_{12}$alkyl, $R_{11}$ is $C_4$–$C_{18}$alkyl, phenyl or —$(CH_2)_a$—CO—O$R_{12}$, a is 1 or 2, and $R_{12}$ is $C_1$–$C_{18}$alkyl.

2. A product according to claim 1, wherein $R_1$ is hydrogen or $C_1$–$C_{12}$alkyl, $R_2$ is $C_1$–$C_{18}$alkyl or phenyl, $R_3$ is hydrogen or $C_1$–$C_6$alkyl, $R_4$, $R^*_4$, $R_5$ and $R^*_5$ are hydrogen, $C_4$–$C_{18}$alkyl, cyclohexyl, benzyl, α-methylbenzyl or αα-dimethylbenzyl, and $R_6$ is hydrogen, methyl, allyl or benzyl.

3. A product according to claim 1, wherein $R_1$ is hydrogen or $C_1$–$C_4$alkyl, $R_2$ is $C_1$–$C_{18}$alkyl, and $R_3$ is hydrogen or $C_1$–$C_4$alkyl.

4. A product according to claim 1, wherein $R_1$ and $R_3$ are hydrogen or methyl, and $R_2$ is $C_1$–$C_{12}$alkyl.

5. A product according to claim 1, wherein $R_4$, $R^*_4$, $R_5$, and $R^*_5$ are hydrogen.

6. A product according to claim 1, wherein the molar ratio of compound of formula II: compound of formula III is from 5:95 to 95:5.

7. A product according to claim 6, wherein the molar ratio is from 70:30 to 30:70.

8. A product according to claim 6, wherein the molar ratio is from 70:30 to 95:5.

9. A product according to claim 6, wherein the molar ratio is from 80:20 to 90:10.

10. A product according to claim 1, wherein the compound of formula I is used in an amount of 0.5 to 4 mol per mol of the mixture of the compounds of formulae II and III.

11. A product according to claim 10, wherein the compound of formula I is used in an amount of 1 to 2 mol per mol of the mixture of the compounds of formulae II and III.

12. A product according to claim 1, wherein the catalyst is selected from the group consisting of the Brønsted acids, Lewis acids, aluminium silicates, ion exchange resins, zeolites, naturally occuring sheet silicates and modified sheet silicates.

13. A product according to claim 12, wherein the Brønsted or Lewis acid is used in an amount of 0.002–10% mol, based on the mixture consisting of formulae II and III, and the aluminium silicates, ion exchange resins, zeolites, naturally occuring sheet silicates or modified sheet silicates are used in an amount of 1–50% by weight, based on the mixture of the compounds of formulae II and III.

14. A product according to claim 1, wherein the catalyst is a naturally occuring sheet silicate ("acid clay") of the bentonite or montmorillonite type.

15. A product according to claim 14, wherein 5–20% by weight of catalyst is used.

16. A composition comprising

A) an organic material susceptible to light-induced, thermal and/or oxidative degradation, and B) at least one product according to claim 1.

17. A composition according to claim 16, wherein the organic material is a natural, semi-synthetic or synthetic polymer, or a functional fluid.

18. A composition according to claim 17, wherein the organic material is a lubricant or a machining fluid or hydraulic fluid.

19. A process for stabilising organic material against oxidative, thermal and/or light-induced degradation, which comprises adding or applying to said material at least one product according to claim 1 as stabiliser.

20. A process according to claim 19 for stabilising natural, semi-synthetic or synthetic polymers or functional fluids.

21. A process according to claim 20 for stabilising synthetic polymers or lubricants, machining fluids or hydraulic fluids.

22. A process for the preparation of a composition, which comprises reacting an olefin of formula $$R_1R_2C=CHR_3 \quad (I)$$

with a mixture of compounds of formulae II and III

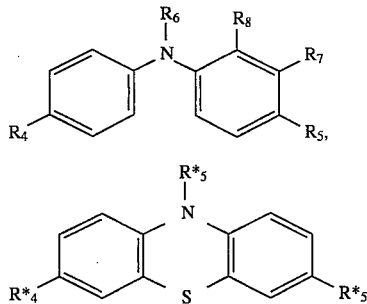

(II)

(III)

in the presence of an acid catalyst, wherein
$R_1$ is hydrogen, $C_1$–$C_{25}$alkyl or phenyl,
$R_2$ is $C_1$–$C_{25}$alkyl, benzyl or phenyl,
$R_3$ is hydrogen or $C_1$–$C_{12}$alkyl,
$R_4$, $R^*_4$, $R_5$ and $R^*_5$ are each independently of one another hydrogen, $C_1$–$C_{25}$alkyl, $C_5$–$C_{12}$cycloalkyl, benzyl, α-methylbenzyl or α,α-dimethylbenzyl, and
$R_6$ and $R^*_6$ are each independently of the other hydrogen, $C_1$–$C_{18}$alkyl, $C_3$–$C_4$alkenyl, benzyl or a radical of formula —CH($R_9$)—CH($R_{10}$)—S—$R_{11}$, and
$R_7$ and $R_8$ are hydrogen, or together form a divalent group

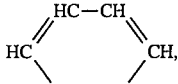

$R_9$ and $R_{10}$ are each independently of the other hydrogen, phenyl or $C_1$–$C_{12}$alkyl,
$R_{11}$ is $C_4$–$C_{18}$alkyl, phenyl or —(CH$_2$)$_a$—CO—OR$_{12}$,
a is 1 or 2, and
$R_{12}$ is $C_1$–$C_{18}$alkyl.

* * * * *